United States Patent [19]

Shortt et al.

[11] Patent Number: 4,678,778

[45] Date of Patent: Jul. 7, 1987

[54] TRITHIOPHOSPHONATE INSECTICIDES

[75] Inventors: Alexandra B. Shortt, Houston, Tex.; William G. Haag, Pleasant Hill, Calif.

[73] Assignee: Stauffer Chemical Company, Westport, Conn.

[21] Appl. No.: 898,544

[22] Filed: Aug. 21, 1986

Related U.S. Application Data

[63] Continuation of Ser. No. 704,814, Feb. 25, 1985, abandoned.

[51] Int. Cl.⁴ .................... A01N 57/02; C07F 9/40
[52] U.S. Cl. ...................... 514/141; 558/203; 558/204
[58] Field of Search ............ 514/141; 558/203, 204

[56] References Cited

U.S. PATENT DOCUMENTS 4,258,038 3/1981 Strong .................... 558/214

Primary Examiner—Anton H. Sutto
Attorney, Agent, or Firm—Joel G. Ackerman

[57] ABSTRACT

Compounds for insecticidal control, having the formula

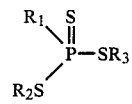

in which $R_1$ is methyl or ethyl; $R_2$ is $C_3$–$C_5$ alkyl or bromo-$C_4$-alkyl and $R_3$ is $C_1$–$C_4$ bromoalkyl or 2,2,2-trifluoroethyl, together with insecticidal compositions containing such compounds, and methods for controlling insects.

18 Claims, No Drawings

TRITHIOPHOSPHONATE INSECTICIDES

This is a continuation of application Ser. No. 704,814, filed Feb. 25, 1985, now abandoned.

This invention relates to a series of trithiophosphonate insecticides having the formula

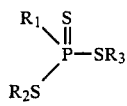

in which $R_1$ is methyl or ethyl; $R_2$ is $C_3$–$C_5$ alkyl or bromo-$C_4$-alkyl and $R_3$ is $C_1$–$C_4$ bromoalkyl or 2,2,2-trifluoroethyl, together with insecticidal compositions containing such compounds, and methods for their use in controlling insects.

Preferably, $R_2$ is a branched alkyl group, most preferably a branched butyl group such as tertiary butyl or secondary butyl.

The term "insects" as used herein refers to the broad and commonly understood usage rather than to those creatures which in the strict biological sense are classified as insects, and includes, in addition to those belonging to the class Insecta, some classes of acarids such as spiders, mites, ticks, and the like, particularly mites.

As will be seen from the data which follows, the compounds of this invention demonstrate activity in controlling various types of insects, for both foliar and soil application, and particularly houseflies, mites and Diabrotica. Several of the compounds show excellent activity as soil insecticides, for controlling soil-borne insects.

The compounds of the present invention may be prepared in general by a two-step process represented by the following reactions:

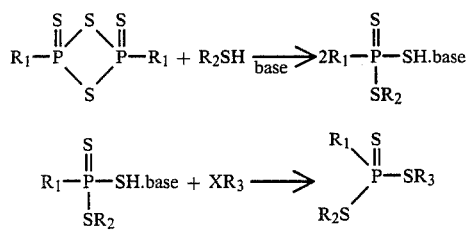

in which X is a halogen (chloro, bromo, or iodo, providing it is more reactive than the bromo or fluoro-substituted site or sites of group $R_3$).

In the first step the appropriate alkyl thionosphosphine sulfide is reacted with two equivalents of a desired mercaptan in the presence of a base to produce a trithioic acid salt. In the second step, the trithioic acid salt is reacted with the appropriate bromoalkyl or trifluoroethyl halide.

The starting alkyl thionophosphine sulfide for Reaction 1 may be obtained by the procedure described in P. E. Newallis, et. al., *Journal of Organic Chemistry*, 1962, Vol. 27, p. 3829.

The first step (Reaction 1) is advantageously carried out at a temperature of from about −40° C. to about 150° C., preferably from about 0° C. to about 70° C., in an organic solvent in the presence of a base, particularly a tertiary amine. Suitable solvents include aromatic hydrocarbons such as benzene or toluene, ethers such as diethyl ether or tetrahydrofuran, and ketones such as acetone. Suitable tertiary amines include triethylamine, dimethylaniline, diethylaniline, and pyridine. Inorganic bases such as sodium hydroxide could be used in this step, but are less desirable as the resulting salts are less soluble in the solvents utilized. As the reaction is exothermic, the base is preferably added dropwise when operating on the laboratory scale. The product may be recovered by evaporating or distilling off the solvent.

The second step (Reaction 2) is conducted in an organic solvent such as that utilized in the first reaction, at a temperature of from about 20° C. to about 130° C., preferably from about 20° C. to 70° C. The product may be recovered by evaporating or distilling off the solvent, and purification by either chromatography or distillation.

The following represent examples of the preparation of compounds of this invention.

EXAMPLE 1

Preparation of S-(t-butyl)-S-(3-bromobutyl)Ethylphosphonotrithioate (Compound 1 herein)

(a) In a flask were mixed 4.73 grams (g) (0.019 mole) of ethylthionophosphine sulfide, 3.43 g (0.038 mole) of t-butyl mercaptan and tetrahydrofuran. Then, 3.85 g (0.038 mole) of triethylamine was added dropwise. The mixture was stirred at room temperature for 1 hour, then refluxed 15 minutes and cooled.

(b) To the mixture was added 4.10 g (0.019 mole) of 1,3-dibromobutane. The mixture was refluxed for 2 days, then cooled and the solvent stripped off. The mixture was extracted with ether, washed twice with water and dried over $MgSO_4$. Solvent was stripped off and the mixture separated by liquid chromatography. Two fractions were recovered. One was identified by nuclear magnetic resonance and mass spectroscopy as 1,3-di-(S-t-butylethylthiophosphonothioato)butane, $n_D^{30}$ 1.5941.

The second fraction, $n_D^{30}$ 1.5692, was similarly identified as the desired product.

EXAMPLE 2

Preparation of S-(sec-butyl)S(2,2,2-trifluoroethyl)ethylphosphonotrithioate (Compound 2 herein)

(a) The triethylamine salt of S-(sec-butyl)ethylphosphonotrithioic acid was prepared as follows: 14.0 g (0.056 mole) of ethyl thionophosphine sulfide was dissolved in tetrahydrofuran; then 11.2 g (0.124 mole) of sec-butyl mercaptan was added, all at once. Then, 11.3 g (0.112 mole) triethylamine was added dropwise. The mixture was stirred at room temperature, then refluxed for 15 minutes. The solvent was removed in vacuo, leaving the acid salt (24.1 g, 68% of theoretical yield) as a semi-solid.

(b) 9.46 g (0.03 mole) of the salt prepared in step (a) and 12.6 g (0.06 mole) 1-iodo-2,2,2-trifluoroethane were mixed in tetrahydrofuran at room temperature. The mixture was stirred at room temperature under an argon blanket for 2 hours, then refluxed for several hours, with monitoring by gas chromatography and thin-layer chromatography. When monitoring showed reaction had terminated, heating was stoppered and the product cooled. It was then washed with ether and water and dried over $MgSO_4$. Ether was removed in vacuo and the product filtered. The resulting liquid was analyzed by gas chromatography and mass and nuclear magnetic spectroscopy, which confirmed the structure.

The following Table I depicts representative compounds of this invention, which may be prepared by the process previously described.

TABLE I $$\begin{array}{c} R_1 \diagdown \overset{S}{\underset{\|}{P}} -SR_3 \\ R_2S \diagup \end{array}$$

| Compound Number | $R_1$ | $R_2$ | $R_3$ |
|---|---|---|---|
| 1 | ethyl | t-butyl | 3-bromobutyl |
| 2 | ethyl | sec-butyl | $CH_2CF_3$ |
| 3 | ethyl | n-propyl | $CH_2CF_3$ |
| 4 | ethyl | 1,1-dimethylpropyl | $CH_2CF_3$ |
| 5 | ethyl | isopropyl | $CH_2CF_3$ |
| 6 | ethyl | n-propyl | 3-bromobutyl |
| 7 | ethyl | 2-methylbutyl | $CH_2CF_3$ |
| 8 | ethyl | 3-methylbutyl | $CH_2CF_3$ |
| 9 | ethyl | sec-butyl | bromomethyl |
| 10 | ethyl | 3-bromobutyl | 3-bromobutyl |
| 11 | ethyl | 1,1-dimethylpropyl | 3-bromobutyl |
| 12 | ethyl | n-butyl | 3-bromopropyl |
| 13 | methyl | t-butyl | 3-bromobutyl |

Structures of the compounds in table I were confirmed by mass spectroscopy. The following data was obtained.

| Compound Number | M+ ion | M-halogen | M-alkyl |
|---|---|---|---|
| 1 | 348 (−) | 269 (+) | 213 (+) |
| 2 | 296 (+) | (−)$^a$ | 240 (+) |
| 3 | 282 (+) | (−)$^a$ | 240 (+) |
| 4 | 310 (−)$^b$ | (−)$^a$ | 240 (+) |
| 5 | 282 (+) | (−)$^a$ | 240 (+) |
| 6 | 335 (+) | 255 (+) | 292 (+) |
| 7 | 310 (+) | (−)$^a$ | 240 (+) |
| 8 | 310 (+) | (−)$^a$ | 240 (+) |
| 9 | 306 (+) | 227 (+) | 250 (+) |
| 10 | 426$^c$ | 247 (+) | 259 (+) |
| 11 | 362 (+) | 283 (+) | 292 (+) |
| 12 | 334 (+) | 255 (+) | 278 (+) |
| 13 | 334 (−)$^b$ | 255 (+) | 278 (−)$^d$ |

$^a$CF$_3$ groups do not usually lose halogen
$^b$M + 1 iso very strong
$^c$molecular weight too high to survive in the inlet system
$^d$M + 1 alkyl very strong

INSECTICIDAL EVALUATION TESTS

The compounds in Table I above were tested by insecticidal activity using the following testing procedures. LD-50 values, based on the results of these tests, and calculated according to dosage-mortality curves, are expressed in Table II.

Housefly [*Musca domestica*]:

(a) Contact: Test compounds were diluted in acetone and aliquots pipetted onto the bottom of aluminum dishes. To insure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1-2 days old. The cages were covered on the bottom with cellophane and on the top with tulle netting, and each contained a sugar-water saturated cotton plug for maintenance of the flies. Mortality was recorded after 48 hours. Test levels ranged from 100 μg/25 female houseflies downward. The LD-50 values are expressed below in Table II under the heading "HF-C", in terms of μg of the test compound per 25 female flies.

(b) Fumigant: Test compounds were diluted in acetone and aliquots pipetted onto 55 mm filter paper discs in the bottom of aluminum dishes. Immediately after the acetone had completely evaporated the dishes were placed in circular cardboard cages (volume—285 ml) containing 25 female houseflies. The cages were sealed on both ends with cellophane and each contained a sugar-water saturated cotton plug for maintenance of the flies. A piece of netting was placed over the aluminum dish in the cage in such a way that the flies were unable to come into direct contact with the chemically treated filter paper. Mortality was recorded after 48 hours. Test levels ranged from 100 μg/25 female houseflies downward. The LD-50 values are expressed in the following Table I under the heading "HF-F", in terms of μg of the test compound per 25 female houseflies per 285 ml volume of the test container.

Black Bean Aphid [*Aphis fabae* (Scop.)]:

Nasturtium plants (Tropaeolum sp.) approximately 5 cm tall, were transplanted into sandy loam soil in small cups and infested with 25-50 black bean aphids of mixed ages. Twenty-four house later they were sprayed to the point of runoff with 50-50 acetone-water solutions of the test compounds. Treated plants were held in the greenhouse and mortality was recorded after 48 hours. Test concentrations ranged from 0.05% downward. The LD-50 values are expressed below in Table II under the heading "BA-C" in terms of percent of the test compound in the sprayed solution.

Tobacco Budworm [*Heliothis virescens* (Fabricius)]:

(a) Contact: Test compounds were diluted in a 50-50 acetone-water solution. Cotton (Gossypium sp.) cotyledons were immersed in the test solutions for 2-3 seconds and placed on a wire screen to dry. The dried leaves were placed in petri dishes containing a moistened piece of filter paper and infested with 5 second-instar tobacco budworm larvae. The dishes were placed in a high humidity chamber for 5 days, and percent mortality of the larvae recorded. Test concentrations ranged from 0.1% downward. The LD-50 values are expressed below in Table II under the heading "TBW-C" in terms of percent of the test compound in the solution.

(b) Eggs: Paper towel patches of 2-day old eggs of the tobacco budworm were dipped in acetone solutions of the test compounds and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LD-50 values are expressed below in Table II under the heading "TBW-E" in terms of percent of the test compound in the solution.

Western Spotted Cucumber Beetle Larvae [*Diabrotica undecimpunctata undecimpunctata* (Mannherheim)]:

Ten grams of moist potting soil was placed in a plastic cup. Test compounds were dissolved in acetone or another appropriate solvent. A 0.05 ml aliquot of the test sample, diluted to the desired concentration, was added to the soil. The cup was capped and the soil was mixed on a vortex mixer for approximately 15 seconds. An indentation was made on the surface of the soil and approximately 50 Diabrotica eggs were added. The eggs were covered with soil and maintained at room temperature (approximately 70° F. or 21° C.). Four days later a section of Romaine lettuce (*Latuca sativa*) leaf was placed in the treated cups. One week later the cups were examined for live larvae. Test concentrations ranged from 25 ppm downward. The LD-50 values are expressed below in Table II under the heading "Diabrotica" in terms of ppm of the test compound in the soil.

Beet Armyworm (*Spodoptera exigua*):

Test compounds were diluted in a 50-50 acetone-water solution. Young leaves of sugar beets (*Beta vulgaris*) were immersed in the test solutions for 2–3 seconds and placed on a wire screen to dry. The dried leaves were placed in petri dishes containing a moistened filter paper and infested with five second-instar beet armyworm larvae. The dishes were placed in a high humidity chamber. Mortality of the larvae was recorded five days later. Test concentrations ranged from 0.1% downward. The LD-50 values are expressed below in Table II under the heading "BAW" in terms of percent of the test compound in solution.

Cabbage Looper [*Trichoplusia ni* (Hubner)]:

Test compounds were diluted in a 50-50 acetone-water solution. Cotyledons of hyzini squash (*Calabacita abobrinha*), approximately 1×1.5 inches, were immersed in the test solutions for 2–3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 5 days later. Test concentrations ranged from 0.1% downward. The LD-50 values are expressed below in Table II under the heading "CL" in terms of percent of the test compound in this solution.

Aster Leafhopper [*Macrosteles fascifrona* (Stal)]:

Oat seedlings (Avena sp.) were grown in a commercial potting soil in plastic cups. When the plants were approximately 10 cm tall they were thinned to 3 plants per cup and dipped for 2–3 seconds in 50-50 acetone-water solutions of the test compounds. When the plants had dried, a clear plastic tube was placed over them and the bottom end pressed into the cup. Ten aster leafhopper adults/nymphs were then placed in each tube and the tops of the tubes covered with white organdy cloth. Mortality counts were made after 48 hours. Test concentrations ranged from 0.05% downward. The LD-50 values are expressed below in Table II under the heading "LH" in terms of percent of the test compound in the solution.

German Cockroach [*Blatella germanica* (Linn.)]:

Test compounds were diluted in a 50-50 acetone-water solution. Two ml of the solution was sprayed through a hand spray gun into circular cardboard cages containing 10 one-month old German cockroach nymphs. The test cages were covered on the bottom with cellophane and on the top with tulle netting. Percent mortality was recorded 4 days later. Test concentrations ranged from 0.1% downward. The LD-50 values are expressed below in Table II under the heading "GR" in terms of percent of the test compound in the sprayed solution.

Lygus Bug [*Lygus hesperus* (Knight)]:

Test compounds were diluted in a 50-50 acetone-water solution. Two ml of the solution was sprayed through a hand-spray gun into circular cardboard cages containing 1 green bean pod and 10 adult lygus bugs. The test cages were covered on the bottom with cellophane and on the top with tulle netting. Percent mortality was recorded 48 hours later. Test concentrations ranged from 0.05% downward. The LD-50 values are expressed below in Table II under the heading "LB" in terms of percent of the test compound in the sprayed solution.

Systemic Assay on Black Bean Aphid [*Aphis fabae* (Scop.)]

Nasturtium plants (Tropaeolum sp.), approximately 5 cm tall, were transplanted into 400 grams of sandy loam soil in one pint containers. Test chemicals were dissolved in acetone and aliquots diluted in 50–60 ml of water. The treated water was poured onto the surface of the soil and allowed to thoroughly soak in. The treated plants were infested with 25–50 black bean aphids of mixed ages and held in the greenhouse. Mortality was recorded after three days. Test concentrations ranged from 10 ppm down to that at which 50% mortality occurs. The LD-50 values are expressed in Table II under the heading "BA(S)" in terms of ppm of the test compound in the soil.

Systemic Assay on Aster Leafhopper

Oat seedlings (Avena sp.) were grown in a commercial potting soil in small cups. When the plants were approximately 10 cm tall, they were thinned to three plants per cup and 2.5 cc of 50-50 acetone-water solutions of the test chemicals were poured in the soil of each cup. Then a clear plastic tube was placed over the plants and the bottom end pressed into the cup. Ten aster leafhopper adults/nymphs were then placed in each tube and the tops of the tubes covered with white organdy clutch. Mortality counts were made after 48 hours. Test concentrations in the soil range from 10 ppm downward. The LD-50 values are expressed below in Table II under the heading "LH-S" in terms of ppm of the test compound in the soil.

Acaricidal Evaluation Test

The two-spotted mite (2SM) [*Tetranychus urticae* (Koch)] was employed in tests for miticides. The test procedure was as follows:

Pinto bean plants (Phaseolus sp.) approximately 10 cm tall, were transplanted into sandy loam soil in 3-inch clay pots and thoroughly infested with two-spotted mites of mixed ages and sexes. Twenty-four hours later the infested plants were inverted and dipped for 2–3 seconds in 50-50 acetone-water solutions of the test compounds. Treated plants were held in the greenhouse, and 7 days later mortality was determined for both adult mites and the nymphs hatching from eggs which were on the plants at the time of treatment. Test concentrations ranged from 0.05% downward. The LD-50 values are expressed below in Table II under the headings "2SM-A" (i.e., adults) and "2SM-E" (i.e., eggs) in terms of percent concentration of the test compound in the solution.

TABLE II

| Cmpd. | HF, ug | BA | 2-SM | TBW, % |
|---|---|---|---|---|
| ($LD_{50}$) | | | | |

TABLE II -continued

| No. | C | F* | C, % | S, ppm | A, % | E, % | C | E |
|---|---|---|---|---|---|---|---|---|
| | | | | (LD$_{50}$) | | | | |
| 1 | 32 | 100 | 0.002 | 1 | 0.001 | 0.003 | 0.002 | 0.01 |
| 2 | 28 | 7.1 | 0.05 | — | >0.05 | >0.05 | >0.1 | 0.007 |
| 3 | 25 | >100 | 0.03 | — | 0.03 | >0.05 | <0.1 | <0.1 |
| 4 | 3 | 3 | 0.03 | 6 | 0.05 | >0.05 | 0.1 | 0.06 |
| 5 | <100 | — | 0.002 | — | 0.05 | >0.05 | >0.1 | 0.07 |
| 6 | 27 | >100 | 0.03 | — | 0.0003 | 0.0006 | 0.006 | 0.1 |
| 7 | <100 | — | 0.03 | — | >0.05 | >0.05 | >0.1 | >0.1 |
| 8 | <100 | — | 0.05 | — | >0.05 | >0.05 | >0.1 | >0.1 |
| 9 | <100 | — | 0.05 | — | 0.003 | 0.003 | 0.07 | 0.008 |
| 10 | 100 | >100 | 0.006 | — | 0.003 | 0.01 | <0.1 | <0.1 |
| 11 | <100 | — | 0.0006 | 10 | <0.05 | <0.05 | 0.007 | >0.1 |
| 12 | 100 | >100 | >0.05 | — | 0.002 | 0.03 | 0.1 | 0.1 |
| 13 | 35 | >100 | 0.0006 | 3 | 0.001 | 0.006 | 0.03 | 0.01 |

| Cmpd. No. | BAW, % | CD, % | LH, % | LH-S ppm | GR, % | LB, % | Diabrotica, ppm (soil) |
|---|---|---|---|---|---|---|---|
| 1 | 0.07 | 0.005 | 0.003 | 6 | 0.03 | 0.005 | 7.5 |
| 2 | 0.07 | 0.01 | 0.03 | 6 | — | — | 0.3 |
| 3 | — | — | >0.05 | 2 | — | — | 0.3 |
| 4 | 0.1 | 0.08 | — | — | >0.1 | >0.05 | 3 |
| 5 | — | — | — | — | — | — | 0.4 |
| 6 | >0.05 | 0.007 | — | — | — | — | 7.5 |
| 7 | — | — | — | — | — | — | 3 |
| 8 | — | — | — | — | — | — | 7.5 |
| 9 | 0.1 | 0.07 | — | — | 0.01 | 0.008 | 3 |
| 10 | >0.1 | >0.1 | — | — | — | — | <25 |
| 11 | 0.03 | 0.006 | — | — | — | — | >25 |
| 12 | >0.1 | >0.1 | — | — | — | — | >25 |
| 13 | 0.006 | 0.006 | — | — | — | — | 3 |

Key:
C = Contact Test
F = Fumigant Test
S = Systemic Test
E = Test on eggs
A = Test on adults
*Per 85 ml volume container In practice, a pure compound can be used as an insecticde. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Eamples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcined diatomaceous earth, calcium carbonate, silica, kieselguhr, clays, etc.; ground synthetic minerals such as various silicates and alumino-silicates and ground vegetable products such as bark, cornmeal, sawdust, cellulose powder and the like. Compositions containing sorptive clays may produce degradation of the active ingredient; accordingly such compositions will usually contain a stabilizer, e.g., a glycol.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of akali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1–50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. Such compounds may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 112 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Component | | Weight % |
|---|---|---|
| Composition A: Granular Solid | | |
| Compound 1 | | 10 |
| attapulgite clay granules | | 85 |
| triethylene glycol | | 5 |
| | Total | 100% |
| Composition B: Wettable Powder | | |
| Compound 2 | | 80 |
| wetting agent (sodium dialkyl-naphthalene sulfonate) | | 1 |
| dispersing agent (sodium lignosulfonate) | | 4 |
| diluent (aluminum magnesium silicate) | | 15 |
| | Total | 100% |
| Composition C: Dilute Solution | | |
| Compound 3 | | 5 |
| solvent (xylene) | | 95 |

| Component | Weight % |
| --- | --- |
| Total | 100% |
| Composition D: Emulsifiable Concentrate | |
| Compound 4 | 50 |
| Emulsifier (blend of metal sulfonates and polyoxyethylene ethers) | 10 |
| solvent (xylene) | 40 |
| Total | 100% |
| Composition E: Concentrated Solution | |
| Compound 5 | 90 |
| solvent (xylene) | 10 |
| Total | 100% |

What is claimed is:

1. A compound having the formula

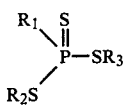

in which $R_1$ is methyl or ethyl; $R_2$ is $C_3$–$C_5$ alkyl or mono-bromo-$C_4$-alkyl and $R_3$ is $C_1$–$C_4$ mono-bromoalkyl or 2,2,2-trifluoroethyl.

2. A method for controlling insects comprising applying to said insect or to a locus at which control is desired an insecticidally effective amount of a compound according to claim 1.

3. A compound according to claim 1 in which $R_3$ is 3-bromobutyl.

4. A compound according to claim 1 in which $R_3$ is 2,2,2-trifluoroethyl and $R_2$ is $C_3$–$C_4$ branched alkyl.

5. A compound according to claim 1 in which $R_1$ is ethyl, $R_2$ is t-butyl and $R_3$ is 3-bromobutyl.

6. A compound according to claim 1 in which $R_1$ is ethyl, $R_2$ is sec-butyl and $R_3$ is 2,2,2-trifluoroethyl.

7. A compound according to claim 1 in which $R_1$ is ethyl, $R_2$ is n-propyl and $R_3$ is 2,2,2-trifluoroethyl.

8. A compound according to claim 1 in which $R_1$ is ethyl, $R_2$ is 1,1-dimethylpropyl and $R_3$ is 2,2,2-trifluoroethyl.

9. A compound according to claim 1 in which $R_1$ is ethyl, $R_2$ is isopropyl and $R_3$ is 2,2,2-trifluoroethyl.

10. A compound according to claim 1 in which $R_1$ is ethyl, $R_2$ is n-propyl and $R_3$ is 3-bromobutyl.

11. A compound according to claim 1 in which $R_1$ is ethyl, $R_2$ is 2-methylbutyl and $R_3$ is 2,2,2-trifluoroethyl.

12. A compound according to claim 1 in which $R_1$ is ethyl, $R_2$ is 3-methylbutyl and $R_3$ is 2,2,2-trifluoroethyl.

13. A compound according to claim 1 in which $R_1$ is ethyl, $R_2$ is sec-butyl and $R_3$ is 2-bromomethyl.

14. A compound according to claim 1 in which $R_1$ is ethyl, $R_2$ is 3-bromobutyl and $R_3$ is 3-bromobutyl.

15. A compound according to claim 1 in which $R_1$ is ethyl, $R_2$ is 1,1-dimethylpropyl and $R_3$ is 3-bromobutyl.

16. A compound according to claim 1 in which $R_1$ is ethyl, $R_1$ is n-butyl and $R_3$ is 3-bromopropyl.

17. A compound according to claim 1 in which $R_1$ is methyl, $R_2$ is t-butyl and $R_3$ is 3-bromobutyl.

18. An insecticidal composition comprising:
(a) an insecticidally effective amount of a compound according to claim 1; and
(b) an inert diluent or carrier.

* * * * *